(12) United States Patent
Evans et al.

(10) Patent No.: US 6,646,008 B1
(45) Date of Patent: Nov. 11, 2003

(54) TREATMENT OF DISEASE STATES WHICH RESULT FROM NEOPLASTIC CELL PROLIFERATION USING PPAR-γ ACTIVATORS AND COMPOSITIONS USEFUL THEREFOR

(75) Inventors: Ronald M. Evans, La Jolla, CA (US); Peter Tontonoz, Los Angeles, CA (US); Laszlo Nagy, Debrecen (HU)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/331,535

(22) PCT Filed: Dec. 29, 1997

(86) PCT No.: PCT/US97/24190

§ 371 (c)(1), (2), (4) Date: Feb. 22, 2000

(87) PCT Pub. No.: WO98/29113

PCT Pub. Date: Jul. 9, 1998

Related U.S. Application Data

(60) Provisional application No. 60/034,813, filed on Dec. 31, 1996.

(51) Int. Cl.[7] ..................... A61K 31/19; A61K 31/557; A61K 31/44; A61K 31/205; A61K 31/12
(52) U.S. Cl. ..................... 514/573; 514/342; 514/356; 514/690
(58) Field of Search ................................ 514/342, 356, 514/690, 573

(56) References Cited

U.S. PATENT DOCUMENTS 5,814,647 A * 9/1998 Urban et al. ........... 514/252.05

OTHER PUBLICATIONS

Kato et al., "Antitumor Activity of delta–7 Prostaglandin A1 and deta–12 Prostaglandin J2 in Vitro and in Vivo", 1986, Cancer Research, vol. 46, No. 7, p. 3538–3542.*

Boehm et al., "Design and Synthesis of Potent Retinoid X Receptor Selective Ligands that Induce Apoptosis in Leukemia Cells", 1995, Journal of Medicinal Chemistry, vol. 38, p. 3146–3155.*

* cited by examiner

*Primary Examiner*—Theodore J. Criares
(74) *Attorney, Agent, or Firm*—Stephen E. Reiter; Foley & Lardner

(57) ABSTRACT

In accordance with the present invention, it has been discovered that PPARγ is expressed consistently in tissues associated with each of a variety of disease states which result from neoplastic cell proliferation. It has further been discovered that maximal activation of PPARγ with exogenous ligand promotes terminal differentiation of primary cells which are otherwise subject to neoplastic cell proliferation. In accordance with another aspect of the invention, it has been discovered that RXR-specific ligands are also potent agents for induction of differentiation of cells expressing the PPARγ/RXRα heterodimer, and that simultaneous treatment of cells subject to neoplastic cell proliferation with a PPARγ-selective ligand, in combination with an RXR-specific ligand, results in an additive stimulation of differentiation. Thus, the effect of neoplastic cell proliferation can be ameliorated by treatment of cells undergoing neoplastic cell proliferation with PPARγ agonists, optionally in the further presence of RXR agonists, thereby blocking further proliferation thereof. Accordingly, compounds and compositions which are useful for the treatment of a variety of disease states which result from neoplastic cell proliferation have been identified and are described herein.

12 Claims, 2 Drawing Sheets

Cell cycle analysis of HL-60 cells (day3)

control 9-cisRA

LG268

PG-J2

LG268 + PG-J2

TREATMENT OF DISEASE STATES WHICH RESULT FROM NEOPLASTIC CELL PROLIFERATION USING PPAR-γ ACTIVATORS AND COMPOSITIONS USEFUL THEREFOR

This application claims benefit of application Ser. No. 60/034,813 filed Dec. 31, 1996.

FIELD OF THE INVENTION

The present invention relates to methods for the treatment of disease states which result from neoplastic cell proliferation. In another aspect, the present invention relates to compounds and compositions which are useful for carrying out the above-referenced methods.

BACKGROUND OF THE INVENTION

Neoplastic cell proliferation is the underlying cause of a wide variety of diseases, e.g., breast cancer, leukemia, colon cancer, prostate cancer, and the like. Traditional approaches to treatment of neoplastic cell proliferation include surgery, chemotherapy, radiotherapy, and the like, as well as combinations thereof. Unfortunately, conventional methods for the treatment of neoplastic cell proliferation require major invasive procedures, induce a variety of undesirable side effects, and/or lead to complete response in only a small percentage of cases. Thus, for many patients, conventional methods of treatment are largely palliative.

Thus, for example, with respect to Liposarcoma, which is the most common soft tissue malignancy in adults, accounting for at least 20% of all sarcomas in this age group, localized disease is treated primarily with surgery, often in combination with radiotherapy. Metastatic liposarcoma is associated with an extremely poor prognosis, with average five year survival ranging from 70% to 25%, depending on the type of tumor. Unfortunately, conventional chemotherapy for metastatic liposarcoma leads to complete response in only about 10% of cases. Thus, for most liposarcoma patients, conventional chemotherapy is largely palliative.

Induction of terminal differentiation represents a promising alternative to conventional methods of treatment for certain malignancies. For example, the retinoic acid receptor alpha (RARα), which plays an important role in the differentiation and malignant transformation of cells of myelocytic lineage, has been used as a target for intervention in acute promyelocytic leukemia. Indeed, differentiation therapy with all-trans retinoic acid has become the standard of care for this disease. In view of this success, it has been speculated that nuclear receptors that regulate growth and differentiation of other cell types may also represent potential targets for differentiation therapy.

Accordingly, the development of effective, non-invasive methods for treating a variety of disease states which result from neoplastic cell proliferation would represent a significant advancement in the therapeutic arts.

BRIEF DESCRIPTION OF THE INVENTION

In accordance with the present invention, we have discovered that PPARγ is expressed consistently in tissues associated with each of a variety of disease states which result from neoplastic cell proliferation. It has further been discovered that maximal activation of PPARγ with exogenous ligand promotes terminal differentiation of primary cells which are otherwise subject to neoplastic cell proliferation. Thus, cells undergoing neoplastic cell proliferation can be induced to differentiate, thereby blocking further proliferation thereof.

In accordance with the present invention, it has still further been discovered that RXR-specific ligands are also potent agents for induction of differentiation of cells expressing the PPARγ/RXRα heterodimer, and that simultaneous treatment of cells subject to neoplastic cell proliferation with a PPARγ-selective ligand, in combination with an RXR-specific ligand, results in an additive stimulation of differentiation. Accordingly, according to the invention, there have been identified compounds and compositions which are useful for the treatment of a variety of disease states which result from neoplastic cell proliferation.

DETAILED DESCRIPTION OF THE INVENTION

Figure 1:
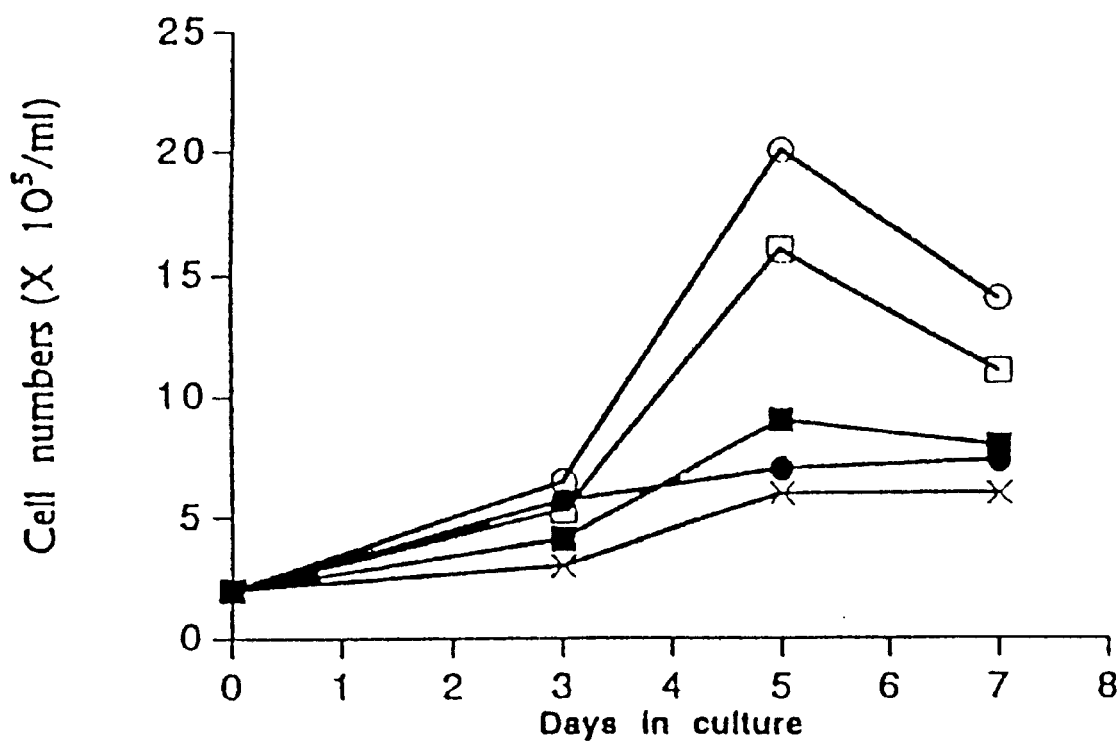
FIG. 1 presents growth curves for the growth of HL-60 cells treated with various ligands for PPARγ and/or RXR. In the Figure, open circles represent the control (no ligand addition), darkened circles represent administration of 9-cis retinoic acid (9-cis RA), open boxes represent administration of LG268, darkened boxes represent administration of prostaglandin J2 and "X" represents co-administration of LG268 and PG-J2.

In accordance with the present invention, there are provided methods for the treatment of subjects suffering from disease states which are the result of neoplastic cell proliferation of cells which express PPAR-γ, said method comprising administering to said subject an amount of a therapeutic composition effective to ameliorate the effect of neoplastic cell proliferation on said cells, wherein said therapeutic composition comprises at least one PPAR-γ activator in a pharmaceutically acceptable carrier therefor. Optionally, therapeutic compositions employed in the practice of the present invention can also contain at least one retinoid X receptor (RXR) selective agonist. Invention methods can also be used in a prophylactic manner, i.e., to prevent the onset of disease states which are the result of neoplastic cell proliferation of cells which express PPAR-γ.

A variety of disease states have been discovered to be the result of neoplastic cell proliferation of cells which express PPAR-γ, and thus are amenable to treatment (and/or prevention) according to the present invention. Such disease states include, for example, breast cancer, myelogenous leukemia, colon cancer, prostate cancer, liposarcomas, and the like.

A variety of PPAR-γ activators are suitable for use in the practice of the present invention. Thus, for example, aromatic compounds bearing at least one eteroatom-containing cyclic moiety (e.g., thiazolidinediones), PPARγ-selective prostaglandins, and the like, are contemplated for use in the practice of the present invention.

Exemplary PPARγ activators contemplated for use in the practice of the present invention include aromatic compounds bearing at least one heteroatom-containing cyclic moiety. Such compounds can be described broadly with reference to the general structure I:

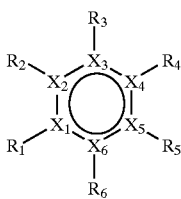

wherein:

each of $X_1$, $X_2$, $X_3$, $X_4$, $X_5$, and $X_6$ is independently carbon, nitrogen, oxygen or sulfur, with the proviso that at least three of the atoms forming the ring are carbon, $R_1$ is alkyl, substituted alkyl, alkenyl, substituted alkenyl, alkynyl, substituted alkynyl, aryl, substituted aryl, alkylaryl, substituted alkylaryl, alkenylaryl, substituted alkenylaryl, alkynylaryl, substituted alkynylaryl, arylalkyl, substituted arylalkyl, arylalkenyl, substituted arylalkenyl, arylalkynyl, substituted arylalkynyl, poly(alkylene oxide), substituted poly(alkylene oxide), poly(alkylene sulfide), substituted poly(alkylene sulfide), poly(alkylene amine), substituted poly(alkylene amine), —OR, —SR or —NR$_2$, wherein each R is independently alkyl, substituted alkyl, alkenyl, substituted alkenyl, alkynyl, substituted alkynyl, aryl, substituted aryl, alkylaryl, substituted alkylaryl, arylalkyl, substituted arylalkyl, poly(alkylene oxide), substituted poly(alkylene oxide), poly(alkylene sulfide), substituted poly(alkylene sulfide), poly(alkylene amine) or substituted poly(alkylene amine); with $R_1$, having in the range of 2 up to 15 carbon atoms being preferred;

$R_2$ is hydrogen, alkyl, substituted alkyl, alkenyl, substituted alkenyl, alkynyl, substituted alkynyl, aryl, substituted aryl, alkylaryl, substituted alkylaryl, alkenylaryl, substituted alkenylaryl, alkynylaryl, substituted alkynylaryl, arylalkyl, substituted arylalkyl, arylalkenyl, substituted arylalkenyl, arylalkynyl, substituted arylalkynyl, oxyalkyl, poly(alkylene oxide) or substituted poly(alkylene oxide); with $R_2$ having in the range of 1 up to about 15 carbon atoms being preferred;

$R_3$ is hydrogen, hydroxy, halogen, alkoxy, lower alkyl, substituted lower alkyl, alkenyl, substituted alkenyl, alkynyl or substituted alkynyl; with $R_3$ having in the range of 0 up to about 6 carbon atoms being preferred;

$R_4$ is hydrogen, formyl, acyl, lower alkyl or substituted lower alkyl; with $R_4$ having in the range of 0 up to about 4 carbon atoms being preferred;

$R_5$ is hydrogen, hydroxy, lower alkoxy, lower alkyl, substituted lower alkyl, alkenyl, substituted alkenyl, alkynyl, substituted alkynyl or halogen; with $R_5$ having in the range of 0 up to about 6 carbon atoms being preferred; and $R_6$ is hydrogen, hydroxy, lower alkoxy, lower alkyl, substituted lower alkyl, alkenyl, substituted alkenyl, alkynyl, substituted alkynyl or halogen; with $R_6$ having in the range of 0 up to about 6 carbon atoms being preferred.

Those of skill in the art recognize that the core ring of structure I can be any one of a number of different aromatic or pseudo-aromatic structures, e.g., a benzene ring, a pyridine ring, a pyrazine, an oxazine, and the like.

As employed herein, "lower alkyl" refers to straight or branched chain alkyl groups having in the range of about 1 up to 4 carbon atoms; "alkyl" refers to straight or branched chain alkyl groups having in the range of about 1 up to 12 carbon atoms; "substituted alkyl" refers to alkyl groups further bearing one or more substituents such as hydroxy, alkoxy (of a lower alkyl group), mercapto (of a lower alkyl group), halogen, trifluoromethyl, cyano, nitro, amino, carboxyl, carbamate, sulfonyl, sulfonamide, heteroatom-containing cyclic moieties, substituted heteroatom-containing cyclic moieties, and the like.

As employed herein, "alkenyl" refers to straight or branched chain hydrocarbyl groups having at least one carbon-carbon double bond, and having in the range of about 2 up to 12 carbon atoms and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "alkenylaryl" refers to alkenyl-substituted aryl groups and "substituted alkenylaryl" refers to alkenylaryl groups further bearing one or more substituents as set forth above.

As employed herein, "alkynylaryl" refers to alkynyl-substituted aryl groups and "substituted alkynylaryl" refers to alkynylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "poly(alkylene oxide)" refers to compounds having the general structure:

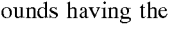

wherein each R' is independently hydrogen or lower alkyl, x falls in the range of 1 up to about 4 and y falls in the range of 2 up to about 8; "substituted poly(alkylene oxide)" refers to poly(alkylene oxide) groups further bearing one or more substituents as set forth above.

As employed herein, "poly(alkylene sulfide)" refers to compounds having the general structure:

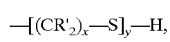

wherein R', x and y are as defined above; "substituted poly(alkylene sulfide)" refers to poly(alkylene sulfide) groups further bearing one or more substituents as set forth above.

As employed herein, "poly(alkylene amine)" refers to compounds having the general structure:

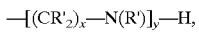

wherein R', x and y are as defined above; "substituted poly(alkylene amine)" refers to poly(alkylene amine) groups further bearing one or more substituents as set forth above.

As employed herein, "acyl" refers to alkyl-carbonyl species.

As employed herein, "halogen" or "halo" refers to fluoro substituents, chloro substituents, bromo substituents or iodo substituents.

In a presently preferred aspect of the present invention, "$R_1$" of Formula I is selected from:

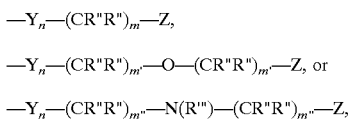

wherein:

Y is —O— or —S—, n is 0 or 1, each R" is independently hydrogen, lower alkyl, substituted lower alkyl, hydroxy, lower alkoxy, thioalkyl, halogen, trifluoromethyl, cyano, nitro, amino, carboxyl, carbamate, sulfonyl or sulfonamide, R'" is hydrogen, lower alkyl or substituted allkyl, m falls in the range of 1 up to 15, each m' falls independently in the range of 1 up to 8, each m" falls independently in the range of 0 up to 12, and Z is a heteroatom-containing cyclic moiety, a substituted heteroatom-containing cyclic moiety, cyano, nitro, amino, carbamate, —$OR^a$, wherein $R^a$ is H, alkyl, alkenyl, alkynyl, acyl or aryl; —$C(O)R^b$, wherein $R^b$ is H, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, alkenylaryl, substituted alkenylaryl, alkynylaryl, substituted alkynylaryl, arylalkyl, substituted arylalkyl, arylalkenyl, substituted arylalkenyl, arylalkynyl, substituted arylalkynyl, heterocyclic, substituted heterocyclic or trifluoromethyl; —$CO_2R^c$, wherein $R^c$ is H, alkyl, alkenyl, alkynyl or aryl; —$SR^a$, —$S(O)R^a$, —$S(O)_2R^a$ or —$S(O)_2NHR^a$, wherein each $R^a$ is as defined above, and the like.

As employed herein, "heteroatom-containing cyclic moiety" refers to cyclic (i.e., 5-, 6- or 7-membered ring-containing) groups containing one or more heteroatoms (e.g., N, O, S, or the like) as part of the ring structure, and having in the range of 1 up to about 14 carbon atoms; and "substituted heteroatom-containing cyclic moiety" refers to heterocyclic groups further bearing one or more substituents as set forth above. Examples of heteroatom-containing cyclic moieties include furans, thiophenes, pyrroles, pyrazoles, diazoles, triazoles, tetrazoles, dithioles, oxathioles, oxazoles, isoxazoles, thiazoles, isothiazoles, oxadiazoles, oxatriazoles, dioxazoles, oxathiazoles, pyrans, pyrones, dioxins, pyridines, pyrimidines, pyrazines, pyridazines, piperazines, diazines, triazines, oxazines, isoxazines, oxathiazines, oxadiazines, morpholines, azepins, oxepins, thiopins, diazepins, benzothiazoles, thiazolidinediones, and the like.

Although the present invention is drawn broadly to the treatment of disease states associated with neoplastic cell proliferation, the treatment of liposarcomas is not contemplated by the above-described method of treatment when I is a thiazolidinedionyl moiety.

It is presently preferred that Z be selected from heteroatom-containing cyclic moieties, with polyheteroatom-containing cyclic moieties being especially preferred. Those of skill in the art can readily identify numerous groups which fall within the definition of "heteroatom-containing cyclic moieties", as set forth herein. Especially preferred are polyheteroatom-containing cyclic moieties, e.g., pyrazoles, diazoles, triazoles, tetrazoles, dithioles, oxathioles, oxazoles, isoxazoles, thiazoles, isothiazoles, oxadiazoles, oxatriazoles, dioxazoles, oxathiazoles, pyridazines, piperazines, diazines, triazines, oxazines, isoxazines, oxathiazines, oxadiazines, morpholines, diazepins, thiazolidinediones, and the like.

Especially preferred compounds employed in the practice of the present invention are those wherein "$R_1$" of Formula I is:

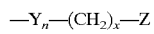

wherein:

Y is —O— or —S—, n is 0 or 1, x falls in the range of 2 up to 12; and

Z is a triazolyl moiety, a tetrazolyl moiety, an oxadiazolyl moiety, an oxatriazolyl moiety, a dioxazolyl moiety, an oxathiazolyl moiety, a triazinyl moiety, an isoxazinyl moiety, an oxathiazinyl moiety, an oxadiazinyl moiety, a thiazolidinedionyl moiety, and the like.

Presently preferred species of $R_1$ include —O—$(CH_2)_4$-[tetrazolinyl moieties] and —O—$(CH_2)_y$-thiazolidenedionyl moieties (wherein y falls in the range of about 2 up to 8).

In another preferred aspect of the present invention, "$R_2$" of Formula I is methyl, ethyl, propyl, butyl, methoxy, ethoxy, propoxy, butoxy, and the like.

In yet another preferred aspect of the present invention, "$R_3$" of Formula I is hydrogen, hydroxy, alkoxy, and the like.

In still another preferred aspect of the present invention, "$R_4$" of Formula I is formyl, acyl, a thiazolidenedionyl moiety, and the like.

In a further preferred aspect of the present invention, "$R_5$" of Formula I is hydrogen.

In a still further preferred aspect of the present invention, "$R_6$" of Formula I is hydrogen.

In yet another preferred aspect of the present invention, at least one of $R_2$, $R_3$, $R_4$, $R_5$ and $R_6$ (in addition to $R_1$) is not hydrogen. It is especially preferred that at least two of $R_2$, $R_3$, $R_4$, $R_5$ and $R_6$ (in addition to $R_1$) are not hydrogen. A plurality of substituents on the ring of structure I is especially preferred when x, m or the sum of (m'+m"), with reference to the backbone of $R_1$, is less than or equal to 6.

Presently preferred species contemplated for use in the practice of the present invention include compounds wherein:

$R_1$ is —O—$(CH_2)_4$-[tetrazolinyl moiety] or —O—$(CH_2)_y$-thiazolidenedionyl moiety, wherein y falls in the range of about 2 up to 8, $R_2$ is hydrogen or lower alkyl, $R_3$ is hydroxy or alkoxy, $R_4$ is acyl or a thiazolidenedionyl moiety; and $R_5$ and $R_6$ are each hydrogen.

The above-described compounds can be readily prepared using a variety of synthetic methods, as are well known by those of skill in the art. For example, many of the above-described compounds can be prepared chemically or enzymatically.

Exemplary PPARγ activators contemplated for use in the practice of the present invention also include PPAR-γ-selective prostaglandins or prostaglandin-like compounds. Such prostaglandins include members of the prostaglandin-$J_2$ family of compounds (e.g., prostaglandin-$J_2$, $\Delta^{12}$-prostaglandin-$J_2$ or 15-deoxy-$\Delta^{12,14}$-prostaglandin-$J_2$), members of the prostaglandin-$D_2$ family of compounds (e.g., prostaglandin-$D_2$), or precursors thereof, as well as compounds having the structure II:

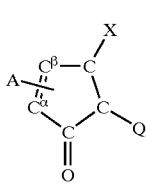

(II)

wherein:
A is selected from hydrogen or a leaving group at the α- or β-position of the ring, or A is absent when there is a double bond between $C^\alpha$ and $C^\beta$ of the ring;
X is an alkyl, substituted alkyl, alkenyl, substituted alkenyl, alkynyl or substituted alkynyl group having in the range of 2 up to 15 carbon atoms; and
Q is an alkyl, substituted alkyl, alkenyl, substituted alkenyl, alkynyl or substituted alkynyl group having in the range of 2 up to 15 carbon atoms.

As employed herein, the term "leaving group" refers to functional groups which can readily be removed from the precursor compound, for example, by nucleophilic displacement, under $E_2$ elimination conditions, and the like. Examples include hydroxy groups, alkoxy groups, tosylates, brosylates, halogens, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

In a presently preferred aspect of the present invention, "X" of Formula II is selected from:
—(CRR)$_m$—Z',
—(CRR)$_{m'}$—C(R)=C(R)—(CRR)$_{m'}$Z', or
—(CRR)$_{m''}$—C≡C—(CRR)$_{m''}$—Z', wherein:
each R is independently H, lower alkyl, substituted lower alkyl, hydroxy, lower alkoxy, thioalkyl, halogen, trifluoromethyl, cyano, nitro, amino, carboxyl, carbamate, sulfonyl or sulfonamide,
m falls in the range of 1 up to 15,
each m' falls independently in the range of 0 up to 12, with the proviso that the total chain length of the alkenyl moiety does not exceed 15 carbon atoms,
each m" falls independently in the range of 0 up to 12, with the proviso that the total chain length of the alkynyl moiety does not exceed 15 carbon atoms, and
Z' is a polar, heteroatom-containing substituent.

Those of skill in the art can readily identify numerous groups which satisfy the requirement that Z' be a polar, heteroatom-containing (i.e., O, N, S, or the like) substituent. Thus, Z' can be selected from cyano, nitro, amino, carbamate, or a substituent having the structure:
—CH$_2$OR', wherein R' is H, alkyl, alkenyl, alkynyl, acyl, aryl, or the like;
—C(O)R", wherein R" is H, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, heterocyclic, substituted heterocyclic or trifluoromethyl,
—CO$_2$R'", wherein R'" is selected from H, alkyl, alkenyl, alkynyl, or the like;
—SR', —S(O)R', —S(O)$_2$R' or —S(O)$_2$NHR', wherein each R' is as defined above, and the like.

Especially preferred compounds employed in the practice of the present invention are those wherein "X" of Formula II is:
—CRR—C(R)=C(R)—(CRR)$_m$—Z', wherein:
each R is independently selected from H, lower alkyl, substituted lower alkyl, hydroxy, alkoxy (of a lower alkyl group), halogen, trifluoromethyl, amino, carboxyl or sulfonyl,
m falls in the range of 1 up to 6, and
Z' is selected from —CH$_2$OH, —CH$_2$OAc, —CO$_2$H, —CO$_2$Me or —CO$_2$Et.

In another preferred aspect of the present invention, "Q" of Formula II is selected from:
=C(R)—[C(R)=C(R)]$_n$—(CRR)$_{n'}$—Z" (III),
=C(R)—[C≡C]$_{n''}$—(CRR)$_{n'}$—Z" (IIIA),
=C(R)—CRR—CR(R')—(CRR)$_{n'}$—Z" (IV),
—[C(R)=C(R)]$_n$—(CRR)$_{n'}$—Z" (V), or
—[C≡C]$_n$—(CRR)$_{n'}$—Z" (VA),
wherein
each R is independently as defined above,
each R' is independently H, lower alkyl, substituted lower alkyl or a leaving group,
Z" is H, lower alkyl or substituted lower alkyl,
n falls in the range of 0 up to 4,
n' falls in the range of 2 up to 12, and
n" falls in the range of 1 up to 3.

Especially preferred compounds contemplated for use in the practice of the present invention include those wherein "Q" of Formula II is selected from:
=C(R)—C(R)=C(R)—(CRR)$_{n'}$—Z" (III),
=C(R)—CRR—CR(R')—(CRR)$_{n'}$—Z" (IV), or
—C(R)=C(R)—CR (R')—(CRR)$_{n'}$—Z" (V), wherein
each R and each R' is independently as defined above,
Z" is H, lower alkyl or substituted lower alkyl, and
n' falls in the range of 1 up to 6.

Presently most preferred compounds for use in the practice of the present invention include those wherein "Q" of Formula II is:
=C(R)—C(R)=C(R)—(CRR)$_{n'}$—Z" (III), wherein
each R is H, lower alkyl or substituted lower alkyl,
n is 1,
n' falls in the range of about 2 up to 6, and
Z" is H or lower alkyl;
or compounds wherein "Q" of Formula II is:
=C(R)—CRR—CR(R')—(CRR)$_n$—Z" (IV) or
—C(R)=C(R)—CR(R')—(CRR)$_{n'}$—Z" (V), wherein each R is H, lower alkyl or substituted lower alkyl,
R' is H, lower alkyl, or an hydroxy group,
n is 1,
n' falls in the range of about 2 up to 6, and
Z" is H or lower alkyl.

Referring to the structural formulae set forth above, prostaglandin-$D_2$ (Pg-D2) is described by Formula II (as set forth above), wherein A is 9-OH, Q is V, each R is hydrogen, R' is hydroxy, Z' is —$CO_2H$, m is 3, Z" is methyl, n is 1 and n' is 4; prostaglandin-$J_2$ (Pg-J2) is described by Formula II, wherein A is absent, Q is V, each R is hydrogen, R' is hydroxy, Z' is —$CO_2H$, m is 3, Z" is methyl, n is 1 and n' is 4; $\Delta^{12}$-prostaglandin-$J_2$ ($\Delta^{12}$-Pg-J2) is described by Formula II, wherein A is absent, Q is IV, each R is hydrogen, R' is hydroxy, Z' is —$CO_2H$, m is 3, Z" is methyl, n is 1 and n' is 4; 15-deoxy-$\Delta^{12,14}$-prostaglandin-$J_2$ (15-deoxy-$\Delta^{12,14}$-Pg-J2) is described by Formula II, wherein A is absent, Q is II, each R is hydrogen, Z' is —$CO_2H$, m is 3, Z" is methyl, n is 1 and n' is 4.

The above-described compounds can be readily prepared using a variety of synthetic methods, as are well known by those of skill in the art. For example, many of the above-described compounds can be prepared chemically or enzymatically, from the naturally occurring precursor, arachidonic acid.

RXR selective lig ontemplated for use in the practice of the present invention include substituted benzoic acids or derivatives thereof (e.g., substituted benzoates), substituted nicotinic acids or derivatives thereof (e.g., substituted nicotinates), substituted carboxylated furans, and the like. Exemplary agonists contemplated for use herein include 4-[1-(3,5,5,8,8-pentamethyl-5,6,7,8-tetrahydro-2-naphthyl)ethenyl]benzoic acid, 1,3-propylene glycol ketal of 4-[1-(5,5,8,8-tetramethyl-5,6,7,8-tetrahydro-2-naphthyl)ethenyl]benzoic acid, methyl 4-[(3,8,8-trimethyl-5,6,7,8-tetrahydronaphthalen-2-yl)carbonyl]benzoate, methyl 4-[(3,5,5-trimethyl-5,6,7,8-tetrahydronaphthalen-2-yl)carbonyl]benzoate, methyl 4-[(1,1,2,3,3,6-hexamethylindan-5-yl)carbonyl]benzoate, methyl 6-[(3,5,5,8,8-pentamethyl-5,6,7,8-tetrahydronaphthalen-2-yl)carbonyl]nicotinate, methyl 4-[1-(3,8,8-trimethyl-5,6,7,8-tetrahydro-2-naphthalen-2-yl)ethenyl]benzoate, methyl 4-[1-(3,5,5-trimethyl-5,6,7,8-tetrahydronaphthalen-2-yl)ethenyl]benzoate, methyl 4-[1-(1,1,2,3,3,6-hexamethylindan-5-yl)ethenyl]benzoate, methyl 6-[1-(3,5,5,8,8-pentamethyl-5,6,7,8-tetrahydronaphthalen-2-yl)ethenyl]nicotinate, 4-[1-(3,8,8-trimethyl-5,6,7,8-tetrahydronaphthalen-2-yl)ethenyl]benzoic acid, 4-[1-(3,5,5-trimethyl-5,6,7,8-tetrahydro-2-naphthalen-2-yl)ethenyl]benzoic acid, 4-[1-(1,1,2,3,3,6-hexamethylindan-5-yl)ethenyl]benzoic acid, 6-[1-(3,5,5,8,8-pentamethyl-5,6,7,8-tetrahydronaphthalen-2-yl)ethenyl]nicotinic acid, methyl 4-[1-methyl-1-(3,5,5,8,8-pentamethyl-5,6,7,8-tetrahydronaphthalen-2-yl)ethyl]benzoate, 4-[2-methyl-1-(3,5,5,8,8-pentamethyl-5,6,7,8-tetrahydronaphthalen-2-yl)ethyl]benzoic acid, 4-[1-methyl-1-(3,5,5,8,8-pentamethyl-5,6,7,8-tetrahydronaphthalen-2-yl)ethyl]benzoic acid, 4-[1-(3,5,5,8,8-pentamethyl-5,6,7,8-tetrahydronaphthalen-2-yl)ethyl]benzoic acid, methyl 4-[1-(3,5,5,8,8-pentamethyl-5,6,7,8-tetrahydronaphthalen-2-yl)cyclopropyl]benzoate, methyl 4-[2-(3,5,5,8,8-pentamethyl-5,6,7,8-tetrahydronaphthalen-2-yl)oxiranyl]benzoate, methyl 6-[1-(3,5,5,8,8-pentamethyl-5,6,7,8-tetrahydronaphthalen-2-yl)cyclopropyl]nicotinate, 4-[1-(3,5,5,8,8-pentamethyl-5,6,7,8-tetrahydronaphthalen-2-yl)cyclopropyl]benzoic acid, 4-[2-(3,5,5,8,8-pentamethyl-5,6,7,8-tetrahydronaphthalen-2-yl)oxiranyl]benzoic acid, 6-[1-(3,5,5,8,8-pentamethyl-5,6,7,8-tetrahydronaphthalen-2-yl)cyclopropyl]nicotinic acid (also referred to in the art as "LG268"), 3,5,5,8,8-pentamethyl-5,6,7,8-tetrahydronaphthalen-2-ol, methyl 4-[(3,5,5,8,8-pentamethyl-5,6,7,8-tetrahydronaphthalen-2-yl)methyl]benzoate, methyl 4-[(3,5,5,8,8-pentamethyl-5,6,7,8-tetrahydronaphthalen-2-yl)oxy]benzoate, 4-[(3,5,5,8,8-pentamethyl-5,6,7,8-tetrahydronaphthalen-2-yl)methyl]benzoic acid, 4-[(3,5,5,8,8-pentamethyl-5,6,7,8-tetrahydronaphthalen-2-yl)oxy]benzoic acid, methyl 2-[(3,5,5,8,8-pentamethyl-5,6,7,8-tetrahydronaphthalen-2-yl)carbonyl]benzoate, methyl 3-[(3,5,5,8,8-pentamethyl-5,6,7,8-tetrahydronaphthalen-2-yl)carbonyl]benzoate, 2-[(3,5,5,8,8-pentamethyl-5,6,7,8-tetrahydronaphthalen-2-yl)carbonyl]benzoic acid, 3-[(3,5,5,8,8-pentamethyl-5,6,7,8-tetrahydronaphthalen-2-yl)carbonyl]benzoic acid, the carboxylated furan derivative referred to as AGN191701 (see Mol. and Cell. Biol. 15:3540–3551 (1995)), and the like.

Presently preferred RXR selective agonists contemplated for use herein include 6-[1-(3,5,5,8,8-pentamethyl-5,6,7,8-tetrahydronaphthalen-2-yl)cyclopropyl]nicotinic acid (LG268) and 4-[1-(3,5,5,8,8-pentamethyl-5,6,7,8-tetrahydronaphthalen-2-yl)ethenyl]benzoic acid.

In accordance with another embodiment of the present invention, there are provided methods for modulating growth of neoplastic cells, wherein said growth is mediated by peroxisome proliferator activated receptor-gamma (PPAR-γ), said method comprising contacting said cells with a composition effective to modulate said growth, wherein said composition comprises at least one PPAR-γ activator in a pharmaceutically acceptable carrier therefor.

As employed herein, the term "modulate" refers to the ability of a modulator for PPARγ to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control.

As employed herein, the phrase "processes mediated by PPARγ" refers to biological, physiological, endocrinological, and other bodily processes which are mediated by receptor or receptor combinations which are responsive to the PPAR-γ agonists described herein (e.g., cell differentiation to produce lipid-accumulating cells, to induce cell differentiation in a variety of other cell types, and the like). Modulation of such processes can be accomplished in vittro or in vivo. In vivo modulation can be carried out in a wide range of mammalian subjects, such as, for example, humans, rodents, sheep, pigs, cows, and the like.

As employed herein, the phrase "amount . . . effective to modulate . . . " refers to levels of compound (or composition) sufficient to provide circulating concentrations high enough to accomplish the desired effect. Such a concentration typically falls in the range of about 10 nM up to 2 $\mu$M; with concentrations in the range of about 100 nM up to 500 nM being preferred. As noted previously, since the activity of different compounds which fall within the definition of structures I and II as set forth above may vary considerably, and since individual subjects may present a wide variation in severity of symptoms, it is up to the practitioner to determine a subject's response to treatment and vary the dosages accordingly.

PPAR-γ-selective agonists (optionally in combination with RXR selective agonists) contemplated for use in the practice of the present invention can be employed for both in vitro and in vivo applications. For in vivo applications, the above-described compounds can be incorporated into a pharmaceutically acceptable formulation for administration. Those of skill in the art can readily determine suitable dosage levels when compounds contemplated for use in the practice of the present invention are so used.

In accordance with another embodiment of the present invention, there are provided compositions comprising at least one PPAR-γ-selective activator (as described herein) and at least one retinoid X receptor (RXR) selective agonist, optionally in a pharmaceutically acceptable carrier. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions.

Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Recent years have seen important advances in the understanding of the molecular basis of adipocyte differentiation. Central to this process is the induction of the adipocyte-selective nuclear receptor, peroxisome proliferator-activated receptor gamma (PPARγ). This receptor and its heterodimeric partner, the retinoid X receptor alpha (RXRa), form a DNA binding complex that regulates transcription of adipocyte-specific genes. Expression and activation of PPARγ in fibroblastic cells triggers the adipocyte gene expression cascade and leads to development of the adipose phenotype.

PPARγ is expressed at high levels in the adipose tissues of mouse and rat (see, for example, Tontonoz et al., in Genes Dev. 8:1224–1234 (1994) and Braissant et al., in Endocrinology 137:354–366(1996)). To determine the tissue distribution of this receptor in humans, Northern analysis of RNA prepared from a variety of human tissues was performed. Human PPARγ is seen to be expressed at highest levels in adipose tissue and at lower levels in several other tissues including lung and kidney. As a control, the blot was also hybridized with cDNA for the adipocyte-specific binding protein aP2. The heart and muscle samples can be seen to contain small amounts of aP2 mRNA, suggesting that these tissues also contain some adipose cells.

Tumorigenesis frequently involves the inactivation or downregulation of genes responsible for initiating and maintaining a differentiated phenotype. As PPARγ appears to play a central role in the adipocyte differentiation process, the expression of this receptor was examined in a series of human liposarcomas. This series included RNA prepared from each of the three major histologic subtypes of liposarcoma; well differentiated/dedifferentiated, myxoid/round cell and pleomorphic. The histologic and cytogenetic characteristics of each tumor is given in Table 5 (see Example 5). For the most part, the well differentiated/dedifferentiated tumors exhibited ring chromosomes and giant marker chromosomes, the myxoid/round cell liposarcomas exhibited the characteristic t(12;16) (13pll) translocation, and the pleomorphic forms exhibited complex rearrangements. Surprisingly, despite their block in differentiation, each liposarcoma examined was found to express high levels of PPARγ RNA, comparable to that of normal fat. These results suggest that most if not all liposarcomas have been transformed at a point in the differentiation process after induction of PPARγ expression. In contrast, PPARγ RNA was not expressed at significant levels in any other type of soft tissue sarcoma examined, including leiomyosarcoma (n=4), fibrosarcoma (n=1), angiosarcoma (n=1), malignant peripheral nerve sheath tumor (MPNS, n=1), or malignant fibrous histiocytoma (MFH, n=1). Thus, PPARγ may be a sensitive marker for distinguishing liposarcoma from other histologic types of soft tissue sarcoma.

Transient transfection experiments were performed to characterize the activation profile of human PPARγ. To eliminate interference from endogenous receptor in the transfected cells, a chimeric PPARγ receptor was utilized that could activate transcription through a heterologous response element (see Forman et al., in Cell 83:803–812 (1995)). This chimeric protein contained the yeast GAL4 DNA binding domain linked to the ligand binding domain of human PPARγ. The GAL4-hPPARγ expression vector was cotransfected into CV-1 cells with a luciferase reporter plasmid containing the GAL4 upstream activating sequence. In this assay, the thiazolidinediones BRL49653, troglitazone and pioglitazone are all seen to be effective activators of human PPARγ.

Liposarcomas have presumably acquired one or more genetic defects that interfere with the course of normal adipocyte development. The observation that PPARγ is expressed consistently in these tumors raised the possibility that the malignant cells might be forced to complete the differentiation program by maximally iactivating the PPARγ pathway. To address this possibility, primary cells isolated from three human liposarcomas were cultured in vitro. Primary cell strains LS857 and LS175 were derived from well differentiated liposarcomas and LS707 was derived from an intermediate grade myxoid/round cell liposarcoma (see Table 5). High grade pleomorphic liposarcoma cells could not be expanded to sufficient numbers to permit studies of differentiation. A primary leiomyosarcoma cell line LM203 was cultured as a control. To confirm that these cultures consisted of malignant tumor-derived cells, cytogenetic analysis was performed. As shown in Table 3, the karyotype of the cells in each culture was characteristic of the parent liposarcoma.

When cultured in the presence of fetal bovine serum and insulin, conditions permissive for adipocyte differentiation, all three cell lines maintain a fibroblastic morphology. LS175 cells contained small amounts of stainable lipid under these conditions. When cultures were treated for 7 days with 10 µM of the PPARγ ligand pioglitazone, the cells readily accumulated lipid and adopted a morphology characteristic of mature culture adipocytes. No lipid accumulation was observed with the LM203 leiomyosarcoma cells, which do not express PPARγ. The degree of morphologically recognizable differentiation varied from 40% in the LS857 cells to 75% in the LS175 cells. After induction for 7 days with thiazolidinedione cells maintained their differentiated morphology even when pioglitazone was withdrawn. This experiment was performed at least twice with each cell strain with quantitatively and qualitatively similar results. Induction of differentiation was also observed with the thiazolidinediones BRL49653 and troglitazone, while no effect was observed with compound 66, the inactive synthetic precursor to BRL49653.

Simultaneous exposure of competent cells to both PPARγ and RXR-specific ligand was investigated to determine if such combination might provide a stronger adipogenic signal than a PPARγ ligand alone. The ability of the RXR-specific ligand LG268 to promote adipocyte differentiation was investigated using NIH-3T3 fibroblasts that express PPARγ from a retroviral vector (see Tontonoz et al, in Cell 79:1147–1156 (1994)). It has previously been shown that wild-type NIH-3T3 cells express RXRα but not PPARγ. NIH-vector and NIH-PPARγ cells were cultured as described in the Examples. At confluence, cells were treated for 7 days with no activator, 1 μM pioglitazone alone, 50 nM LG268 alone, or 5 μM thiazolidinedione and 50 nM LG268. After an additional four days of culture, cells were fixed and stained with oil red O. Data are presented in Table 1 as the range of morphologically recognizable differentiation observed for each line over three separate experiments.

TABLE 1

% lipid containing cells

| cell line | no activator | +pioglitazone | +LG268 | +pioglitazone + LG268 |
|---|---|---|---|---|
| NIH | 0 | 0 | 0 | <1 |
| NIH-PPARγ | 2–5 | 60–70 | 50–65 | >90 |

As shown in Table 1, treatment of confluent NIH-PPARγ cells for 7 days with 50 nM LG268 resulted in significant stimulation of adipocyte differentiation, comparable to that seen with 7 days of treatment with 1 μM pioglitazone alone. Thus simultaneous exposure to both activators resulted in an additive effect. LG268 had no effect on NIH-vector cells, indicating that the adipogenic activity of this compound, like that of pioglitazone, is dependent on the presence of PPARγ. Similar results are obtained with the preadipocyte cell lines 3T3-L1 and 3T3-F442A, which express both PPARγ and RXRα. Northern analysis confirms that pioglitazone and LG268 have an additive effect on the induction of the adipocyte-specific genes aP2 and adipsin in NIH-PPARγ cells. No induction of adipocyte gene expression was observed in NIH-vector cells under similar conditions.

The ability of LG268 to promote differentiation of human liposarcoma cells was then examined. Treatment of LS857 cells for 7 days with 50 nM LG268 led to a significant degree of adipocyte differentiation, similar to that seen with 10 μM pioglitazone alone. When LS857 cells were treated simultaneously with LG268 and a thiazolidinedione (either pioglitazone or BRL449653), an additive effect on differentiation was observed. To further characterize the effects of PPARγ and RXR ligands on liposarcoma cells, the expression of adipocyte-specific markers were examined by Northern blotting. LS857 cells, like the-tumor from which they were derived, express PPARγ mRNA. Treatment of LS857 cells with pioglitazone leads to the induction of two markers of terminal adipocyte differentiation, the MRNAs encoding aP2 and adipsin. Simultaneous treatment with pioglitazone and LG268 results in an additive induction of adipocyte gene expression. In summary, treatment of LS857 cells with thiazolidinediones and RXR-specific retinoids leads to changes in morphology and gene expression consistent with terminal adipocyte differentiation.

Terminal differentiation of white adipocytes in vitro and in vivo is characterized by permanent withdrawal from the cell cycle. A critical question is whether thiazolidinedione-induced differentiation of liposarcoma cells is accompanied by growth arrest. To address this issue, LS857 cells were cultured in the presence or absence of pioglitazone. Following induction of morphologic differentiation, pioglitazone was withdrawn. After 48 hours of continued culture in the absence of pioglitazone, cells were labeled for 48 hours with 5-bromo-2'-deoxyuridine (BrdU). Cells undergoing DNA synthesis during the labeling period should stain positive for BrdU incorporation after fixation and incubation with an enzyme-linked monoclonal antibody (see Examples).

LS857 cells were cultured in the presence or absence of pioglitazone. Following induction of morphologic differentiation, pioglitazone was withdrawn. After 48 hours of continued culture in the absence of pioglitazone, cells were labeled for 48 hours with bromodeoxyuridine, stained using an enzyme-linked monoclonal antibody (see Examples) and visualized microscopically. The number of cells staining positive for BrdU and/or containing visible cytoplasmic lipid is indicated in Table 2.

TABLE 2

| Experiment | # cells counter | # BrdU + (%) | # lipid + (%) | # lipid +/ BrdU + (%) |
|---|---|---|---|---|
| control | 500 | 232 (46) | 0 | NA |
| PIO/LG #1 | 510 | 173 (34) | 204 (40) | 22 (4) |
| PIO/LG #2 | 595 | 156 (26) | 233 (51) | 17 (3) |

In the experiments shown in Table 2 (PIO/LG268#1 and PIO/LG268#2), 26–34% of the cells contained visible cytoplasmic lipid. 40–51% of the cells in this culture stained positive for BrdU incorporation by light microscopy; however, of those cells containing lipid, only 3–4% stain positive for BrdU. When differentiated cultures were trypsinized and replated, lipid-containing cells failed to reenter the cell cycle as determined by BrdU labeling. These results demonstrate the thiazolidinedione-induced differentiation of LS857 cells leads to cell cycle withdrawal.

Termination differentiation of most specialized cell types, including white adipocytes, is linked to cell cycle withdrawal. Tumorigenesis is characterized by a loss of cell cycle control and a concordant block in the differentiation program. It has been demonstrated herein that most human liposarcomas express high levels of the adipocyte regulatory complex PPARγ/RXRα and that PPARγ and RXRα-specific ligands are able to trigger terminal differentiation of primary human liposarcoma cells in vitro. These results suggest that the developmental defect in most liposarcomas is downstream of PPARγ expression, and that in at least some tumor cells this developmental block can be overcome by maximal activation of the PPARγ pathway.

While the precise nature of the developmental defects in liposarcoma is not yet clear, it is likely these defects ultimately lead to the inactivation or antagonism of one or more adipocyte transcriptional regulatory proteins. Members of both the C/EBP and PPAR transcription factor families have been shown to play central complementary roles in adipogenesis in murine models (see, for example, Cornelius et al., in Ann. Rev. Nutr. 14:771–774 (1994), Tontonoz et al., in Curr. Opin. Genet. Dev. 5:571–576 (1995), Freytag et al., in Genes Dev. 8:1654–1663 (1994), Wu et al., in Genes Dev. 9:2350–2363 (1995) and Yeh et al., in Genes Dev 9:168–181 (1995)). Interestingly, the C/EBP family has previously been implicated in the pathogenesis of human myxoid liposarcoma through the characterization of the t(12:16) translocation associated with this tumor. This rearrangement fuses the gene for the C/EBP family member CHOP on chromosome 12 to that of the RNA binding protein TLS on chromosome 16 (see Crozat et al., in Nature 363:640–644 (1993)). CHOP lacks a transcriptional activation domain and has therefore been postulated to function as a dominant negative regulator of other C/EBP proteins. The precise mechanism whereby TLS/CHOP contributes to differentiation arrest and tumorigenesis, however, remains to be elucidated.

The mechanisms by which differentiation is coupled to cessation of cell growth are not fully understood; however, there is mounting evidence that key proteins controlling differentiation interact directly with the cell cycle machinery. For example, the myogenic transcription factor MyoD has been shown to be negatively regulated by cyclin D1-dependent kinase and to induce expression of the cdk inhibitor p21 (see, for example, Halevy et al., in Science 267:1018–1021 (1995) and Skapek et al., in Science 267:1022–1024 (1995)).

The impact of RXR-specific activators on adipocyte differentiation has not previously been addressed. It is demonstrated herein that RXR-specific retinoids can function as adipogenic regulators through activation of the PPARγ/RXRα heterodimer, and that the adipogenic activity of the heterodimer is maximal when both receptors are bound by their respective ligands. Given that PPARγ is likely to be the biologic receptor mediating the insulin-sensitizing effects of the thiazolidinediones, this observation suggests that RXR-specific ligands may also have insulin-sensitizing activity in vivo. Moreover, the insulin-sensitizing effects of thiazolidinedione ligands for PPARγ might be enhanced by simultaneous administration of an RXR-specific ligand.

The results presented herein have important implications for the pharmacologic management of liposarcoma in humans. Liposarcoma is currently managed with surgery and a judicious combination of chemotherapy and radiotherapy. Despite conventional multimodality therapy, anywhere from 25 to 75% of patients with advanced liposarcoma will die from their disease within 5 years. The present results suggest that a combination of the thiazolidinedione class of antidiabetic drugs and RXR-specific retinoids may be useful as a non-toxic alternative to conventional chemotherapy for the treatment of disseminated or locally advanced liposarcoma. Members of the thiazolidinedione class of drugs have undergone extensive preclinical testing as anti-diabetic agents. Troglitazone is currently is phase three clinical trials in the U.S. and studies have supported its usefulness in NIDDM (see Nolan et al., in N. Engl. J. Med. 331:1188–1193 (1994)). Other thiazolidinediones have been approved for clinical use in Japan. Although certain thiazolidinediones have been associated with some degree of toxicity in long-term use as insulin sensitizing agents, this should not preclude their use as antineoplastic agents as conventional chemotherapy is associated with far greater toxicity. The ability of a combination of thiazolidinediones and RXR-specific retinoids to induce differentiation of liposarcoma cells in vi tro strongly suggests that these compounds may also be able to stimulate differentiation and growth arrest of human tumors in vivo.

The invention will now be described in greater detail by reference to the following non-limiting examples.

EXAMPLE 1

Growth of HL-60 Cells in the Presence of Various Ligands

HL-60 cells were plated at a density of $2 \times 10^5$ cells/ml and were treated with:

100 nM 9-cis retinoic acid (9-cis RA; which is both RAR and RXR active), 100 nM LG268 (which is RXR selective), 3 μM prostaglandin J2 (PG-J2; which is PPARγ active), or a combination of 100 nM of LG268 and 3 μM of PG-J2.

Cell numbers were determined after 3, 5 or 7 days of culture, as illustrated in FIG. 1.

The results show that 9-cis RA alone, and PG-J2 alone each inhibit cell growth, while LG268 alone has only a marginal ability to promote cell differentiation. The combination of PG-J2 and LG268, however, shows an enhanced ability to inhibit cell growth.

EXAMPLE 2

Cell Cycle Analysis of HL-60 Cells When Grown in the Presence of Various Ligands HL-60 cells were plated at a density of $2 \times 10^5$ cells/ml and were treated with:

100 nM 9-cis retinoic acid (9-cis RA; which is both RAR and RXR active), 100 nM LG268 (which is RXR selective), 3 μM prostaglandin J2 (PG-J2; which is PPARγ active), or a combination of 100 nM of LG268 and 3 μM of PG-J2.

Figure 2:
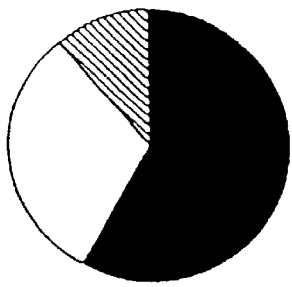
FIG. 2 presents a cell cycle analysis of HL-60 cells when treated with various ligands for PPARγ and/or RXR. In the Figure, the darkened portion of each graph represents that proportion of the cell population in G1 phase, the white portion of each graph represents that proportion of the cell population in S phase, and the striped portion of each graph represents that proportion of the cell population in G2 phase.
Figure 2:
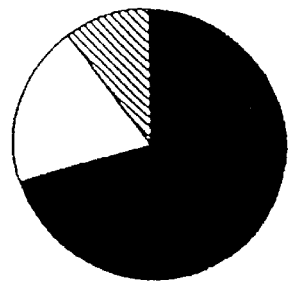
Figure 2:
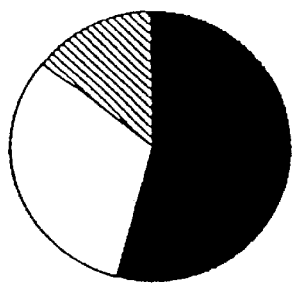
Figure 2:
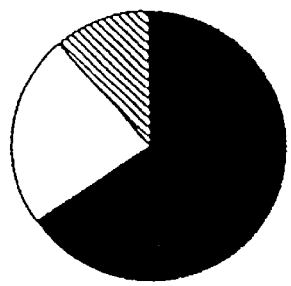
Figure 2:
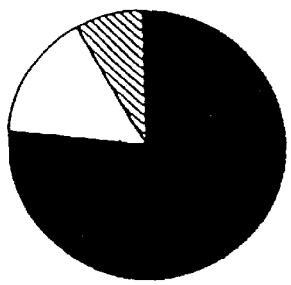

Cell cycle analysis was carried out on day 3 using standard DNA content determination by flow cytometry. Results are presented graphically in FIG. 2, and summarized in Table 3.

TABLE 3

| Sample | Cell Cycle Phase, % | | |
|---|---|---|---|
| | G1 | S | G2 |
| Control | 58.7 | 30.1 | 11.2 |
| 9-cis RA | 70.5 | 19.2 | 10.2 |
| LG268 | 54.5 | 31.1 | 14.4 |
| PG-J2 | 65.9 | 22.6 | 11.5 |
| LG268 + PG-J2 | 76.9 | 15.1 | 8.0 |

The results show that treatment with either 9-cis RA (i.e., induction of the RARU pathway) or PG-J2 (i.e., induction of the PPARγ pathway) inhibits cell cycle progression and leads to the accumulation of cells in G1. Treatment of HL-60 cells with the combination of LG268 and PG-J2 produces a synergistic effect, whereby an increased number of cells accumulate in Gi.

EXAMPLE 3

Synergistic Induction of Differentiation in HL-60 and THP-1 Leukemia Cells When Treated With Ligands for PPARγ and RXRα

HL-60 and THP-1 leukemia cells were seeded at a ensity of $2 \times 10^5$ cells/ml and cultured in RPMI containing 10% charcoal-stripped fetal calf serum. Cells were treated with either vehicle alone, or 10 nM AM580, 100 nM LG268, or 3 μM 15-deoxy-Δ12,14-prostaglandin-J2. After 5 days, cells were incubated with monoclonal antibody to the monocyte-specific differentiation antigen CD14, and analyzed by flow cytometry using a Becton Dickinson FACScan. Median fluorescence values for each culture are presented in Table 4.

TABLE 4

| Sample | median fluorescence |
|---|---|
| A. HL-60 cells | |
| control | 24 |
| AM580 | 26 |
| LG268 | 138 |
| PG-J2 | 47 |
| LG268/PG-J2 | 274 |
| B. THP-1 cells | |
| control | 13 |
| LG268 | 18 |
| PG-J2 | 16 |
| LG268/PG-J2 | 58 |

Inspection of the data presented in Table 4 reveals that the combination of a PPARγ agonist (e.g., PG-J2) and an RXR agonist (e.g., LG268) dramatically increases the proportion of HL-60 and THP-1 cells which respond to a differentiation marker.

EXAMPLE 4

Tissue Samples and Cytogenetics

Normal human tissues, liposarcomas and other soft tissue sarcomas were obtained from surgical cases at the Brigham and Women's Hospital, Boston. All tissue samples were taken from homogeneous and viable portions of the resected sample by the pathologist and frozen within 10 minutes of excision. Hematoxylin and eosin stained sections of each soft tissue sarcoma were reviewed by a single pathologist (C.F.) and classified according to histologic type, grade, mitotic activity and surgical margin. Histologic classification was based solely on morphologic patters recognition using conventional diagnostic criteria. Mitotic activity counts were performed with high power field size of 0.120 mm² and at least 50 high power fields were counted from the most cellular areas of the tumor. for cytogenetic analysis tumors were dissagregated with collagenase and harvested after 3–7 days of culture in T25 flasks (see Fletcher et al., in N. Eng. J. Med. 324:436–443 (1991)). Metaphase cells were analyzed by trypsin-Giemsa (see Seabright in Lancet 2:971–972 (1971)) and quinacrine mustard banding (see Fletcher et al., in Am. J. Pathol. 138:515 (1991)).

EXAMPLE 5

Northern Analysis

Total RNA was prepared from tumors and normal human tissues by guanidium isothiocyanate extraction and CsCl centrifugation. RNA was electrophoresed through formaldehyde-agarose gels, blotted to BioTrans nylon membranes (ICN) and hybridized as directed by the manufacturer. cDNA probes were labeled with [α-$^{32}$-P] -dCTP by the random priming method to a specific activity of at least $10^9$ cpm/μg.

To determine expression of PPARγ mRNA in human liposarcomas and other soft tissue sarcomas, total TNA (15 μg per lane) was isolated from human tumors, electrophoresed through a formaldehyde-containing agarose gel, blotted to nylon and hybridized with $^{32}$P-labeled hPPARγ CDNA as described above. Equivalent amounts of intact RNA were run in each lane as indicated by ethidium bromide staining of the membrane after transfer and hybridization to a 36B4 cDNA probe. The histologic and cytogenetic characteristics of each tumor analyzed are summarized in Table 5.

TABLE 5

| Tumor | Histology | Cytogenetics | Mitotic Index | Cell Culture |
|---|---|---|---|---|
| 107SP | well differentiated liposarcoma | 47–48,XX, +1–2mars | 0.2 | NA |
| 115SP | high grade myxoid/round cell liposarcoma | 80–91,XXXX, t(12;16)(q13;p11)x2 | 6.0 | NA |
| 1165P | high grade liposarcoma with pleomorphic, myxoid, well differentiated areas | ND | 19.8 | NA |
| 200SP | high grade liposarcoma, mixed pleomorphic and round cell | ND | 7.2 | NA |
| 203SP | well differentiated liposarcoma | 48–50,XY, del(16)(q36), +2–4 r | ND | LS175 |
| 204SP | well differentiated liposarcoma | 48,XX,add(7)(136), del(11)(p13), +2 mars | ND | LS857 |
| P144 | well differentiated liposarcoma | 48,XX,+2r | 0 | NA |
| P147 | well differentiated liposarcoma lipoma-like, sclerosing | 46–49,XX, add(9)(q34), +1–2r,+1–2mars | 0 | NA |
| P154 | atypical lipoma/well differentiated liposarcoma | ND | 0 | NA |
| P155 | intermediate grade liposarcoma myxoid > round cell component | 46,XY, t(12;16)(q13;p11) | 1.0 | LS707 |
| P156 | intermediate grade liposarcoma round cell > myxoid component | 49XY,+del(1)(p32), +2,+8, t(12;16)(q13;p11) | 1.0 | NA |
| P158 | well differentiated liposarcoma | ND | 0 | NA |
| P160 | well differentiated liposarcoma with dedifferentiated areas | 43–49,XX, add(1)(q43), −11,−13,−13,+1−3r | 1.1 | NA |

PPARγ is observed to be expressed in multiple histologic types of human liposarcoma, while PPARγ is not expressed in other human soft tissue sarcomas.

EXAMPLE 6

Cell Culture

Primary liposarcoma cells were isolated from selected freshly harvested tumors as described previously (see Sreekantaiah et al., in Am. J. Pathol. 144:1121–1134 (1994) and Fletcher et al., in Am. J. Pathol. 138:515 (1991), as well as references cited therein. Primary cells were plated at a density of at least 2×10⁵ cells/ml and cultured in 60 mm dishes in RPMI containing 15% Cosmic Calf Serum (Hyclone), 20 μg/ml bovine pituitary extract (Collaborative Research) and 5 μg/ml insulin.

PPARγ- and RXR-specific ligands induce expression of markers of terminal adipocyte differentiation in PPARγ-expressing fibroblasts and human liposarcoma cells. NIH-vector, NIH-PPARγ and LS857 cells were cultured as described above. At confluence cells were treated for 7 days with no activator, pioglitazone alone, LG268 alone, or pioglitazone and LG268 as indicated. Total RNA (10 μg per lane) was isolated from, electrophoresed through a formaldehyde-containing agarose gels, blotted to nylon and hybridized with $^{32}$P-labeled human or murine PPARγ, human or murine aP2, and human or murine adipsin cDNA using standard techniques. Equivalent amounts of intact RNA was run in each lane as indicated by ethidium bromide staining of the membrane after transfer and hybridization to a 36B4 cDNA probe.

In order to evaluate the induction of differentiation in human liposarcoma cells by thiazolidinediones and RXR-specific retinoids, LS857 cells were cultured as described above. At confluence, cells were treated for 7 days with no activator, 5 μM thiazolidinedione (BRL 49653) or pioglitazone), 50 nM LG268, or 5 μM thiazolidinedione and 50 nM LG268 as indicated. After an additional four days of culture, cells were fixed and stained with oil red O. Macroscopic view of the 60 mM culture dishes shows that thiazolidinedione alone or LG268 alone stimulate significant lipid accumulation, while simultaneous addition of both thiazolidinedione and LG268 has at least an additive effect on lipid accumulation, stimulating substantially higher levels of lipid accumulation than either agent alone.

EXAMPLE 7

Transfection Assays

The GAL4-hPPARγ expression vector was generously provided by V. K. K. Chaterjee. This construct contains residues 1–147 of GAL4 fused to residues 173–475 of hPPARγ and is driven by the SV40 early promoter (see Greene et al., in Gene Express. 4:281–299 (1995)). CV-1 cells were cultured in DMEM containing 10% resin-charcoal-stripped calf serum. Transfections were performed in phenol free DMEM containing 10% resin-charcoal-stripped fetal calf serum by the lipofection method using DOTAP (Boehringer Mannheim) according to the manufacturer's instructions. After 2 hours, liposomes were removed and cells were cultured for an additional 40 hours in the presence or absence of thiazolidinediones as indicated. Luciferase and B-galactosidase assays were carried out as described previously (see Forman et al., in Cell 83:803–812 (1995)).

An SV40-GAL4/hPPARγ expression vector (100 ng/10$^5$ cells) was cotransfected into CV-1 cells with a UAS$_{GX}$4 TK-LUC reporter plasmid (300 ng/0$_5$ cells) and a CMX-BGAL internal control plasmic (500 ng/10$^5$ cells) as described above. Following transfection cells were treated with indicated concentrations of Pioglitazone (Upjohn), troglitazone (Parke Davis-Warner Lambert), BRL49653 (BIOMOL) and LG268 (Ligand Pharmaceuticals) were dissolved in DMSO and applied to cells in a volume of less than 5 μl. The NIH-PPARγ and NIH-vector cells were derived by retroviral infection as previously described (see Tontonoz et al., in Cell 79:1147–1156 (1994)) and cultured in DMEM containing 10% Cosmic Calf Serum and 5 μg/ml insulin. Differentiated cells were fixed and stained for neutral lipid with oil red 0. BrdU labeling was performed using the 5-bromo-2'-deoxyuridine Labeling and Detection Kit II (Boehringer Mannheim) according to the manufacturer's instructions.

These experiments demonstrate that thiazolidinediones activate PPARγs.

While the invention has been described in detail with reference to certain preferred embodiments thereof, it will be understood that modifications and variations are within the spirit and scope of that which is described and claimed.

That which is claimed is:

1. A method for treating a subject suffering from a disease state which is the result of neoplastic cell proliferation of breast cells which express PPAR-γ, said method comprising administering to said subject an amount of a therapeutic composition effective to ameliorate the effect of neoplastic cell proliferation on said cells, wherein said therapeutic composition comprises at least one PPAR-γ activator in a pharmaceutically acceptable carrier therefor.

2. A method according to claim 1 wherein said PPAR-γ activator is a PPAR-γ-selective prostaglandin or prostaglandin-like compound or precursor thereof.

3. A method according to claim 2 wherein said PPAR-γ-selective prostaglandin is a prostaglandin-J$_2$, a prostaglandin-D$_2$, or a precursor thereof.

4. A method according to claim 3 wherein said prostaglandin-J$_2$ is prostaglandin-J$_2$, Δ$^{12}$-prostaglandin-J$_2$ or 15-deoxy-Δ$^{12,14}$-prostaglandin-J$_2$.

5. A method according to claim 1 wherein said PPAR-γ activator has the structure I, wherein structure I is as follows:

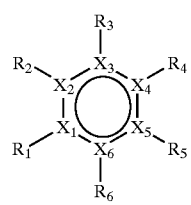

(I)

wherein:
each of $X_1$, $X_2$, $X_3$, $X_4$, $X_5$ and $X_6$ is independently carbon, nitrogen, oxygen or sulfur, with the proviso that at least three of the atoms forming the ring are carbon, $R_1$ is alkyl, substituted alkyl, alkenyl, substituted alkenyl, alkynyl, substituted alkynyl, aryl, substituted aryl, alkylaryl, substituted alkylaryl, alkenylaryl, substituted alkenylaryl, alkynylaryl, substituted alkynylaryl, arylalkyl, substituted arylalkyl, arylalkenyl, substituted arylalkenyl, arylalkynyl, substituted arylalkynyl, poly(alkylene oxide), substituted poly(alkylene oxide), poly(alkylene sulfide), substituted poly(alkylene sulfide), poly(alkylene amine), substituted poly(alkylene amine), —OR, —SR or —NR$_2$, wherein each R is independently alkyl, substituted alkyl, alkenyl, substituted alkenyl, alkynyl, substituted alkynyl, aryl, substituted aryl, alkylaryl, substituted alkylaryl, arylalkyl, substituted arylalkyl, poly(alkylene oxide), substituted poly(alkylene oxide), poly(alkylene sulfide), substituted poly(alkylene sulfide), poly(alkylene amine) or substituted poly(alkylene amine);

$R_2$ is hydrogen, alkyl, substituted alkyl, alkenyl, substituted alkenyl, alkynyl, substituted alkynyl, aryl, substituted aryl, alkylaryl, substituted alkylaryl, alkenylaryl, substituted alkenylaryl, alkynylaryl, substituted alkynylaryl, arylalkyl, substituted arylalkyl, arylalkenyl, substituted arylalkenyl, arylalkynyl, substituted arylalkynyl, oxyalkyl, poly(alkylene oxide) or substituted poly(alkylene oxide);

$R_3$ is hydrogen, hydroxy, halogen, alkoxy, lower alkyl, substituted lower alkyl, alkenyl, substituted alkenyl, alkynyl or substituted alkynyl;

$R_4$ is hydrogen, formyl, acyl, lower alkyl or substituted lower alkyl;

$R_5$ is hydrogen, hydroxy, lower alkoxy, lower alkyl, substituted lower alkyl, alkenyl, substituted alkenyl, alkynyl, substituted alkynyl or halogen; and R₆ is hydrogen, hydroxy, lower alkoxy, lower alkyl, substituted lower alkyl, alkenyl, substituted alkenyl, alkynyl, substituted alkynyl or halogen.

6. A method according to claim 5 wherein "R₁", Formula I is:

wherein:

Y is —O— or —S—, n is 0 or 1, each R" is independently hydrogen, lower alkyl, substituted lower alkyl, hydroxy, lower alkoxy, thioalkyl, halogen, trifluoromethyl, cyano, nitro, amino, carboxyl, carbamate, sulfonyl or sulfonamide, R'" is hydrogen, lower alkyl or substituted allkyl, m falls in the range of 1 up to 15, each m' falls independently in the range of 1 up to 8, each m" falls independently in the range of 0 up to 12, and Z is a heteroatom-containing cyclic moiety, a substituted heteroatom-containing cyclic moiety, cyano, nitro, amino, carbamate, —OR$^a$, wherein R$^a$ is H, alkyl, alkenyl, alkynyl, acyl or aryl; —C(O)R$^b$, wherein R$^b$ is H, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, alkenylaryl, substituted alkenylaryl, alkynylaryl, substituted alkynylaryl, arylalkyl, substituted arylalkyl, arylalkenyl, substituted arylalkenyl, arylalkynyl, substituted arylalkynyl, heterocyclic, substituted heterocyclic or trifluoromethyl; —CO₂R$^c$, wherein R$^c$ is H, alkyl, alkenyl, alkynyl or aryl; —SR$^a$, —S(O)R$^a$, —S(O)₂R$^a$ or —S(O)₂NHR$^a$, wherein each R$^a$ is as defined above.

7. A method according to claim 6 wherein Z is a furan, thiophene, pyrrole, pyrazole, diazole, triazole, tetrazole, dithiole, oxathiole, oxazole, isoxazole, thiazole, isothiazole, oxadiazole, oxatriazole, dioxazole, oxathiazole, pyran, pyrone, dioxin, pyridine, pyrimidine, pyrazine, pyridazine, piperazine, diazine, triazine, oxazine, isoxazine, oxathiazine, oxadiazine, morpholino, azepin, oxepin, thiopin, diazepin, benzothiazole or a thiazolidinedione.

8. A method according to claim 6 wherein Z is a pyrazole, diazole, triazole, tetrazole, dithiole, oxathiole, oxazole, isoxazole, thiazole, isothiazole, oxadiazole, oxatriazole, dioxazole, oxathiazole, pyridazine, piperazine, diazine, triazine, oxazine, isoxazine, oxathiazine, oxadiazine, morpholine, diazepin or a thiazolidinedione.

9. A method according to claim 5 wherein "R₁", of Formula I is:

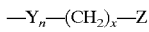

wherein:

Y is —O— or —S—, n is 0 or 1, x falls in the range of 2 up to 12; and

Z is a triazolyl moiety, a tetrazolyl moiety, an oxadiazolyl moiety, an oxatriazolyl moiety, a dioxazolyl moiety, an oxathiazolyl moiety, a triazinyl moiety, an isoxazinyl moiety, an oxathiazinyl moiety, an oxadiazinyl moiety, or a thiazolidinedionyl moiety.

10. A method according to claim 1 wherein said therapeutic composition further comprises at least one retinoid X receptor (RXR) selective agonist.

11. A method according to claim 10 wherein said retinoid X receptor (RXR) selective agonist is a substituted benzoic acid or derivative thereof, a substituted nicotinic acid or derivative thereofor or a substituted carboxylated furan.

12. A method according to claim 10 wherein said retinoid X receptor (RXR) selective agonist is 6-[1-(3,5,5,8,8-pentamethyl-5,6,7,8-tetrahydronaphthalen-2-yl)cyclopropyl]nicotinic acid (LG268).

* * * * *

UNITED STATES PATENT AND TRADEMARK OFFICE
CERTIFICATE OF CORRECTION

PATENT NO.   : 6,646,008 B1                                                                Page 1 of 1
DATED        : November 11, 2003
INVENTOR(S)  : Ronald M. Evans, Peter Tontonoz and Laszlo Nagy It is certified that error appears in the above-identified patent and that said Letters Patent is hereby corrected as shown below:

<u>Column 21,</u>
Line 4, after "$R_1$" insert the word -- of --
Line 16, change "allkyl" to -- alkyl --

Signed and Sealed this

Fourth Day of May, 2004

JON W. DUDAS
*Acting Director of the United States Patent and Trademark Office*